United States Patent [19]

Garner

[11] Patent Number: 4,841,960

[45] Date of Patent: Jun. 27, 1989

[54] METHOD AND APPARATUS FOR INTEROSSEOUS BONE FIXATION

[76] Inventor: Eric T. Garner, 7123 Mountain Grove, San Antonio, Tex. 78250

[21] Appl. No.: 12,838

[22] Filed: Feb. 10, 1987

[51] Int. Cl.$^4$ ................................................. A61F 5/04
[52] U.S. Cl. ............................ 128/92 YF; 128/92 YC; 128/335
[58] Field of Search ........ 128/94 YC, 92 YD, 92 YF, 128/92 YE

[56] References Cited

U.S. PATENT DOCUMENTS

| | | | |
|---|---|---|---|
| 3,807,394 | 4/1974 | Attenborough | 128/92 R |
| 3,862,631 | 1/1975 | Austin | 128/92 R |
| 3,939,828 | 2/1976 | Mohr et al. | 128/92 YC |
| 3,960,147 | 6/1976 | Murray | 128/92 YC |
| 4,026,520 | 5/1977 | Rothfuss et al. | 254/28 |
| 4,434,796 | 3/1984 | Karapetian et al. | 128/335 |
| 4,540,110 | 9/1985 | Bent et al. | 128/92 YC X |

FOREIGN PATENT DOCUMENTS 64726  8/1982  Israel .

OTHER PUBLICATIONS

Bogush, et al., *Instrument for Mechanical Stitiching of Bone*, Central Scientific-Research Institute of Tuberculosis, Central Scientific Research Institute of Stomatology, All-Union Scientific Research and Test Institute of Medical Equipment, Moscow, translated from Meditsinskaya Tekhnika, No. 4, pp. 52-54, Jul.-Aug. 1974, original article submitted Jan. 1, 1973, attached pp. 245-247.

Cranin, et al., The infraorbital rim staple—a new method of treating displaced and comminuted trimalar fractures, 37 J. Oral Surgery 364, 365 (May 1979).

*Primary Examiner*—Robert A. Hafer
*Assistant Examiner*—Kevin G. Rooney
*Attorney, Agent, or Firm*—Richard J. Smith

[57] ABSTRACT

A method and apparatus for interosseous bone fixation. Portions of bone on opposite sides of a fracture are compressed toward each other by inserting the opposite ends of a bone staple into each bone portion and crimping the central portion of the staple. A bone staple having a central web portion adapted to be crimped into substantially an inverted V shape is also disclosed. Various devices for crimping a bone staple are also disclosed.

3 Claims, 8 Drawing Sheets

METHOD AND APPARATUS FOR INTEROSSEOUS BONE FIXATION

BACKGROUND OF THE INVENTION invention relates to a method and apparatus for interosseous bone fixation, including a crimpable bone staple and a crimping device, for stabilizing fractured or cut bones.

The use of orthopedic surgery staples for setting and connecting bone fragments is generally known in the art. Israeli Pat. No. 64,726 discloses a bone staple and staple spreading tool. The staple comprises a central portion and two legs having serrations on the inward side thereof. The cross section of the central portion is less than that of the legs in order to provide a higher resilience to the central portion In its untensioned state, the central portion and two legs are slightly curved in an inward direction. However, when the legs are pulled apart by the spreading tool, the curvature disappears since the three components are straightened The staple is thereafter inserted into bone fragments on opposite sides of a fracture to pull the fragments together as soon as the outwardly directed pulling force on the legs is released. The disclosure of Israeli Pat. No. 64,726 states that the elasticity of the staple material will tend to return the staple to its original shape but that the straightened orientation of the legs and central portion is the shape in which the staple should stay within the bone.

SUMMARY OF THE INVENTION

The present invention provides a crimpable bone staple, a crimping device, and method for achieving interosseous bone fixation. The feet of the staple are positioned within drilled holes on opposite sides of a fracture line and the center of the staple is thereafter crimped, thereby providing compressive forces to the respective bone edges and rigid fixation of the bone portions.

The staple of the present invention comprises a staple body having a web or central portion of reduced thickness relative to the maximum thickness of the remainder of the staple body. Barbed feet are located on each end of the staple body. The staple body may be provided with an angled web to facilitate crimping.

The method for fixating bone fragments comprises the steps of drilling a monocortical or bicortical hole on each side of a bone fracture, inserting the feet of a crimpable bone staple into the drilled holes, crimping the staple web, and compressing the crimped portion of the staple. If the crimped portion of the staple extends outward from the bone, it may be folded downward to lay substantially parallel to the bone.

One embodiment of a crimping device comprises a tool body having a lever pivotally connected thereto. One end of the tool body is adapted to provide a pair of abutments on each end of a crimpable bone staple. One end of the lever arm provides a fulcrum movable intermediate to the abutments. A longitudinal groove within the tool body is adapted to receive a plurality of bone staples. The crimping tool is further provided with spring and plate apparatus for urging the staples toward the forward end of the tool body within the longitudinal groove. The crimping tool is also provided with spring and plate apparatus for retaining the staples within the tool body. The forward end of the lever arm is adapted to urge the forward staple outward through the forward end of the tool body while retaining the remaining staples within the body.

An alternate embodiment of a crimping device comprises a tool body having a trigger activated push rod mounted thereto. The forward end of the push rod defines a pair of abutments while the forward end of the tool body defines a fulcrum. A variation of the foregoing embodiment further comprises a staple cartridge for removable attachment to the tool body. Devices for crimping a single staple are also disclosed.

DETAILED DESCRIPTION OF THE PREFERRED EMBODIMENT

Figure 1:
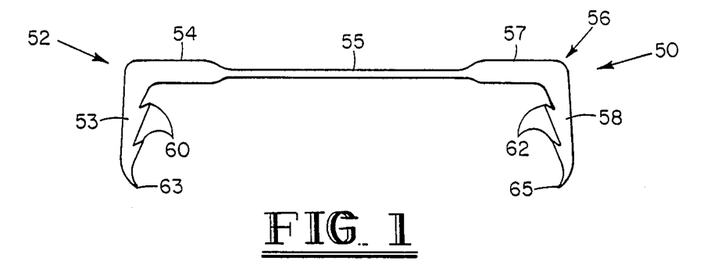
FIG. 1 is a side view of the preferred embodiment of a bone staple.
Figure 2:
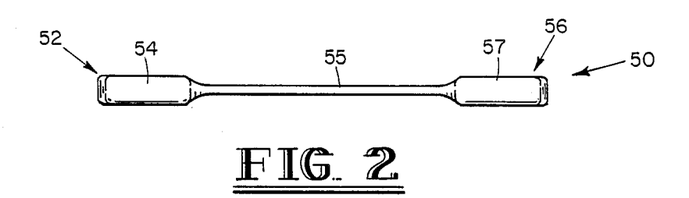
FIG. 2 is a top view of the preferred embodiment of a bone staple.

Referring to FIG. 1 and FIG. 2, the crimpable bone staple 50 of the present invention is illustrated in detail. The staple 50 comprises a first end 52, a central web portion 55, and a second end 56. First end 52 comprises a first foot 53 and a first shoulder 54. Second end 56 comprises a second shoulder 57 and a second foot 58. The central web portion 55 intermediate first end 52 and second end 56 has a cross sectional area which is less than th maximum cross sectional area of the first end 52 or second end 56. Feet 53 and 58 have jagged serrations or barbs 60 and 62, respectively, on the medial side thereof. The tips 63 and 65 of feet 53 and 58, respectively, are preferably pointed and slightly curved inward.

Figure 3:
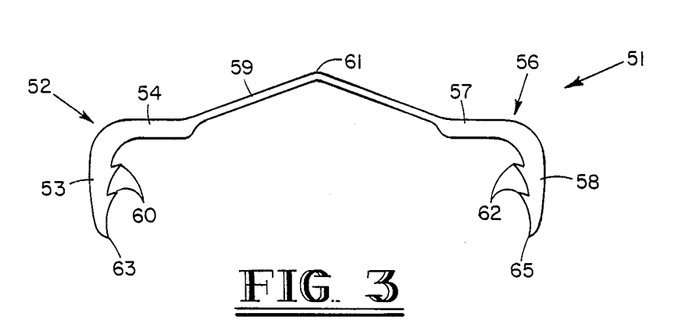
FIG. 3 is a side view of an alternate embodiment of a bone staple.
Figure 4:
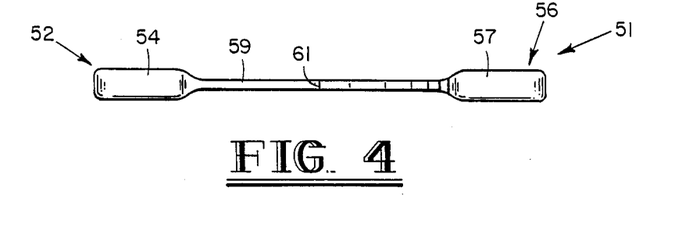
FIG. 4 is a top view of an alternate embodiment of a bone staple.

An alternate embodiment of a crimpable bone staple 51 is illustrated in FIG. 3 and FIG. 4, with like numbers being utilized to identify features discussed in connection with staple 50. The bone staple 51 has an angled web portion 59 having a vertex 61 in approximately the center thereof. The central web portion 59 intermediate first end 52 and second end 56 has a cross sectional area which is less than the maximum cross sectional area of the first end 52 or second end 56. The angled web portion 59 is designed to facilitate crimping of the staple 51 as described hereinbelow.

Staples 50 and 51 are preferably constructed of a unitary piece of stainless steel having a length and gauge (thickness) which is determined by the stress requirements of the bone fixation to which the staple 50 or 51 is to be applied. Further, the thickness of web portions 55 and 59 is preferably reduced relative to the maximum thickness of the remainder of the respective staple body in order t facilitate crimping of the web portions 55 and 59 as described hereinbelow. However, the thickness of web portions 55 and 59 may be substantially equivalent to, or greater than, the maximum thickness of the remainder of the respective staple body, provided the web portions 55 and 59 are crimpable as described hereinbelow. Feet 53 and 58 are substantially perpendicular to shoulders 54 and 57, respectively. Feet 53 and 58 are also substantially perpendicular to web portion 55.

Figure 5:
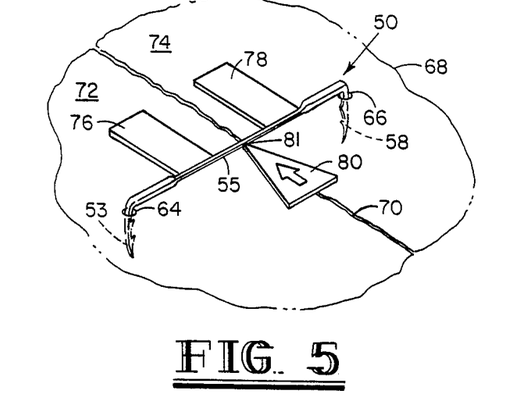
FIGS. 5-8 illustrate steps in the preferred method for interosseous bone fixation.
Figure 6:
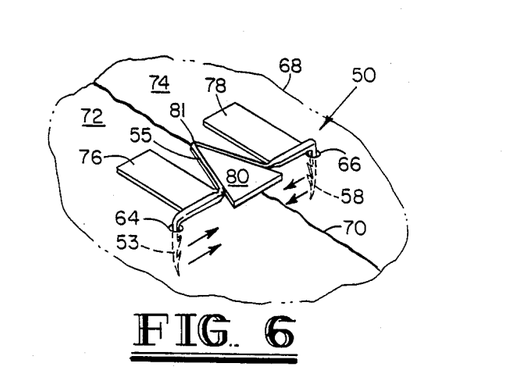
Figure 7:
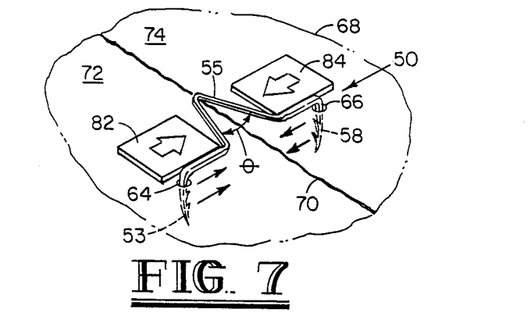
Figure 8:
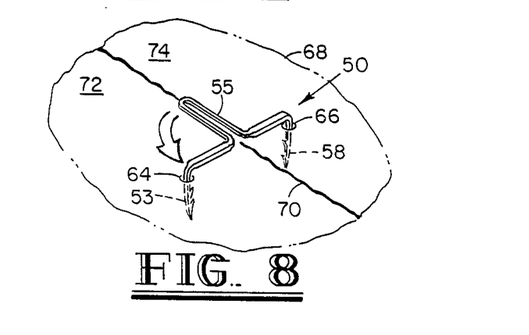

Referring to FIGS. 5–8, the preferred method for interosseous bone fixation is illustrated in detail. A pair of holes 64 and 66 are drilled in a section of bone 68 on opposite sides of, and approximately equal distance from, a fracture line 70. Hole 64 is drilled in a left portion 72 of bone 68 on one side of fracture line 70 and hole 66 is drilled in a right portion 74 of bone 68 on the opposite side of fracture line 70. As illustrated in FIG. 5, the feet 53 and 58 of a staple 50 are thereafter inserted into holes 64 and 66, respectively. A staple crimping device, such as the crimping device 86 described hereinbelow, having a pair of abutments 76 and 78 and a fulcrum 80 having an apex 81, is thereafter utilized to crimp or bend the staple 50, as illustrated in FIG. 6. The apex 81 abuts approximately the center of web 55 and fulcrum 80 moves intermediate to abutments 76 and 78. As further illustrated in FIG. 6, the web 55 of staple 50 is preferably crimped into substantially an inverted "V" shape, substantially parallel to the outer surface of bone 68, thereby urging feet 53 and 58 toward fracture line 70 and compressing the left 72 and right 74 portions of bone section 68 toward each other along fracture line 70, as illustrated by the arrows in FIG. 6. Web 55 is preferably crimped in a plane substantially perpendicular to the plane of feet 53 and 58. As illustrated in FIG. 7, the V-shaped portion of web 55 is thereafter compressed, such as by a plier-type device having jaws 82 and 84, thereby further urging feet 53 and 58 toward fracture line 70 and further compressing the left 72 and right 74 portions of bone 68 toward each other along fracture line 70, as illustrated by the arrows in FIG. 7. The compressed portion of web 55 may thereafter be folded toward one side of fracture line 70, as illustrated by the arrow in FIG. 8. It is to be understood that additional staples 50, as necessary, may be applied to bone 68 along fracture line 70 in a manner as illustrated in FIGS. 5–8. It is also to be understood that the crimped and compressed staple(s) 50 may be removed at the conclusion of the healing process.

Figure 9:
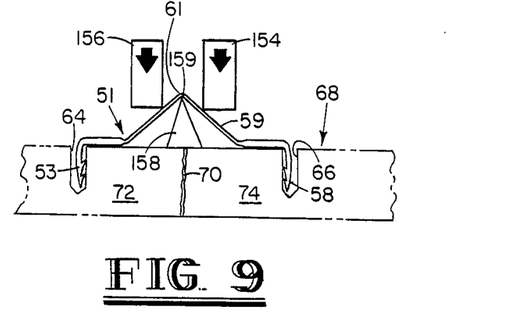
FIGS. 9-12 illustrate steps in an alternate method for interosseous bone fixation
Figure 10:
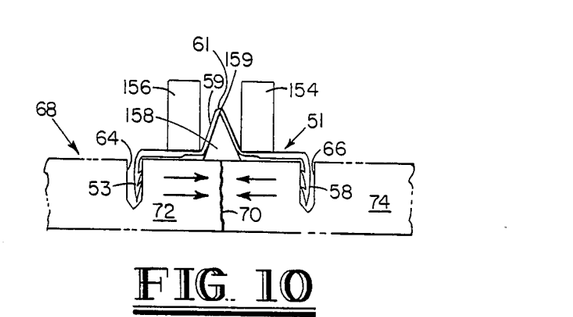
Figure 11:
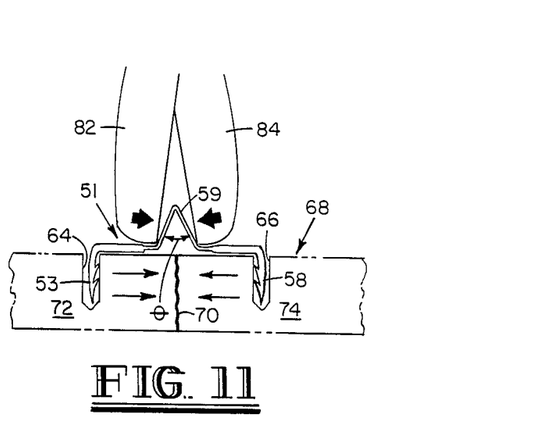
Figure 12:
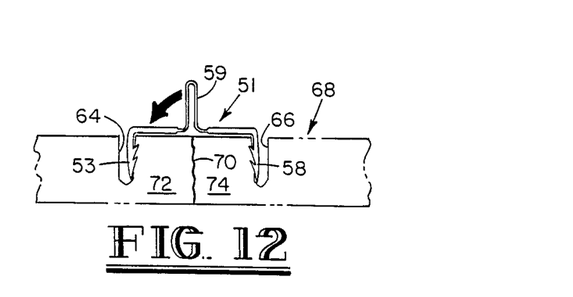

Referring to FIGS. 9–12, an alternate method for interosseous bone fixation is illustrated in detail. A pair of holes 64 and 66 are drilled in a section of bone 68 on opposite sides of, and approximately equal distance from, a fracture line 70. Hole 64 is drilled in a left portion 72 of bone 68 on one side of fracture line 70 and hole 66 is drilled in a right portion 74 of bone 68 on the opposite side of fracture line 70. As illustrated in FIG. 9, the feet 53 and 58 of a staple 51 are thereafter inserted into holes 64 and 66, respectively. A staple crimping device, such as the crimping device 134 described hereinbelow, having a pair of abutments 154 and 156 and a fulcrum 158 having an apex 159, is thereafter utilized to crimp or bend the staple 51, as illustrated in FIG. 10. The apex 159 abuts vertex 61 in approximately the center of web 59 and abutments 154 and 156 move about fulcrum 158 so that fulcrum 158 is intermediate abutments 154 and 156. As further illustrated in FIG. 10, the web 59 of staple 51 is preferably crimped into substantially an inverted "V" shape, substantially perpendicular to the outer surface of bone 68, thereby urging feet 53 and 58 toward fracture line 70 and compressing the left 72 and right 74 portions of bone 68 toward each other along fracture line 70, as illustrated by the arrows in FIG. 10. Web 59 is preferably crimped in substantially the same plane as feet 53 and 58. As illustrated in FIG. 11, the V-shaped portion of web 59 is thereafter compressed, such as by a plier-type device having jaws 82 and 84, thereby further urging feet 53 and 58 toward fracture line 70 and further compressing the left 72 and right 74 portions of bone 68 toward each other along fracture line 70, as illustrated by the arrows in FIG. 11. The compressed portion of web 59 may thereafter be folded downward toward one side of fracture line 70, as illustrated by the arrow in FIG. 12. It is to be understood that additional staple(s) 51, as necessary, may be applied to bone 68 in a manner as illustrated in FIGS. 9–12. It is also to be understood that the crimped and compressed staple(s) 51 may be removed at the conclusion of the healing process.

It is to be understood that holes 64 and 66 will normally be drilled to a depth of approximately 3-4 millimeters (mm) but may be extended deeper in bone 68 as dictated by the length of feet 53 and 58 of the staple 50 or 51. The length of feet 53 and 58 is, in turn, dictated by the stress requirements of the bone fixation to which staple 50 or 51 is to be applied. It is also to be understood that the crimping step illustrated in FIGS. 6 and 10 provides an initial compression of bone portions 72 and 74 toward each other along fracture line 70. Further, the crimping step illustrated in FIGS. 6 and 10 provides substantially equivalent and simultaneous compressive forces to bone portions 72 and 74 in the directions illustrated by the respective arrows on portions 72 and 74. It is also to be understood that the compression step illustrated in FIGS. 7 and 11 provides a second or further compression of bone portions 72 and 74 toward each other along fracture line 70. Further, the compression step illustrated in FIGS. 7 and 11 provides substantially equivalent and simultaneous compressive forces to bone portions 72 and 74 in the directions illustrated by the respective arrows on portions 72 and 74. Further, barbs 60 and tip 63 and barbs 62 and tip 65 are urged into and grip the bone portions 72 and 74, respectively, during the compression of bone portions 72 and 74 toward each other. It is also to be understood that the angle $\theta$ formed by the crimped portions of webs 55 and 59, as illustrated in FIG. 7 and FIG. 11, respectively, will preferably be an acute angle. It is also to be understood that a channel (not shown) may be formed in bone 68 to receive the compressed portion of web 55 or 59 illustrated in FIGS. 8 and 12, respectively. Finally, it is to be understood that for the sake of clarity abutments 76, 78, 154, and 156, fulcrums 80 and 158, and jaws 82 and 84 are merely represented generally in FIGS. 5–12.

Referring to FIGS. 13–17, the crimping tool 86 of the present invention is illustrated in detail. The crimping tool 86 comprises a tool body 88 having a pivotal lever arm or crimper 94 connected thereto by a pivot pin 100. The opposite ends of pin 100 are connected to tool body 88. Pin 100 extends through a passage 101 in lever arm 94. Tool body 88 has a forward end 90 and a rearward end 92. Lever arm 94 has a forward end 96 and a rearward end 98. Tool body 88 has a longitudinal slot 102 in the underside thereof within which to receive the forward end 96 of lever arm 94. Tool body 88 has a longitudinal slot 104 in the top thereof within which to receive the rearward end 98 of lever arm 94. A spring 89 is positioned intermediate bottom 91 of tool body 88 and arm 94 and secured thereto by rivets 93 and 95, respectively.

Figures 13, 16:
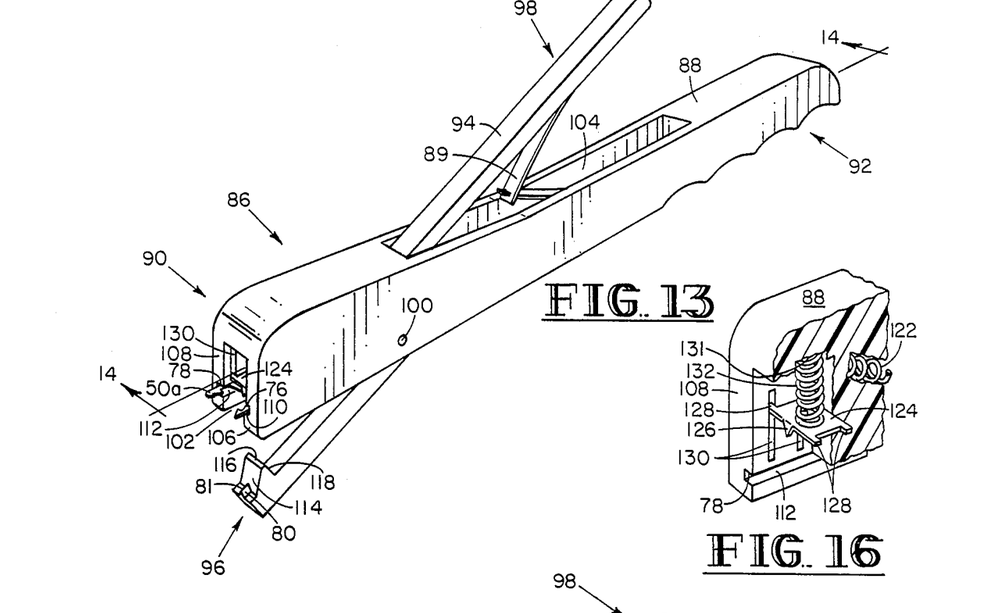
FIG. 13 is a perspective view of the preferred embodiment of a crimping tool.
FIG. 16 is a perspective cut away view of a portion of the preferred embodiment of a crimping tool illustrated in FIG. 13.
Figures 14, 15, 17:
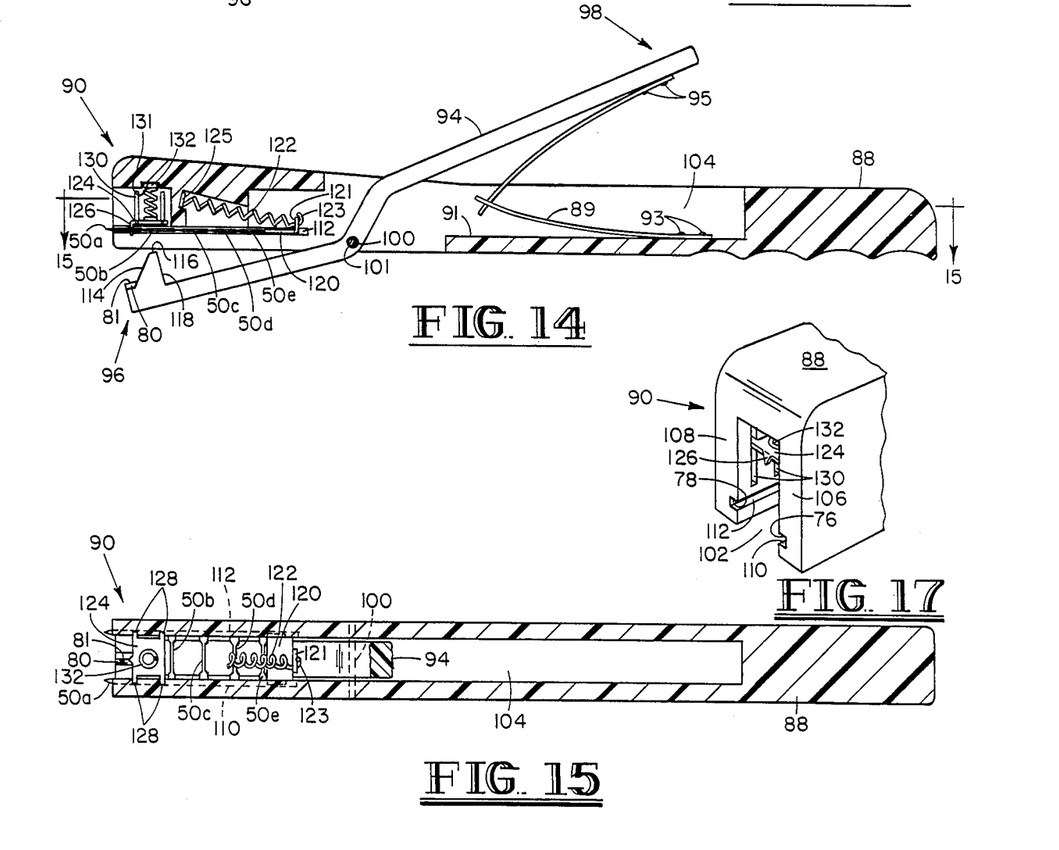
FIG. 14 is a cross-sectional view of the preferred embodiment of a crimping tool taken along section lines 14—14 of FIG. 13.
FIG. 15 is a cross-sectional view of the preferred embodiment of a crimping tool taken along section lines 15—15 of FIG. 14.
FIG. 17 is a perspective view of the forward end of the preferred embodiment of a crimping tool illustrated in FIG. 13.

Referring to FIGS. 13, 15, and 17, the forward end 90 of tool body 88 is provided with a pair of side walls 106 and 108 on opposite sides of slot 102. Side wall 106 is provided with a longitudinal groove 110 within which to receive the end 52 or 56 of a staple 50. Side wall 108 is provided with a longitudinal groove 112 within which to receive the opposite end 56 or 52, respectively, of a staple 50. As illustrated in FIG. 15, grooves 110 and 112 preferably receive the respective ends of a plurality of staples 50a, 50b, 50c, 50d, and 50e, each of which corresponds to staple 50 described hereinabove. As illustrated in FIGS. 13 and 17, grooves 110 and 112 define abutments 76 and 78, respectively, within tool body 88. As illustrated in FIG. 13 and FIG. 14, the forward end 96 of crimper 94 is provided with a fulcrum 80 having an apex 81, a crimper angle or angled camming surface 114, a pin plate abutment surface 116, and a staple retaining surface 118. For purposes of clarity, no staples are shown in FIG. 16 or FIG. 17.

Referring again to FIG. 14 and FIG. 15, the crimping tool 86 is further provided with a staple plate 120 located within grooves 110 and 112 at the rear of the row or column of staples 50a–50e. Staple plate 120 abuts the most rearward staple 50e and the feet of each staple, except forward staple 50a, abut the staple immediately in front thereof. A staple plate spring 122 is appropriately attached on a first end thereof 123 to an upward protrusion 121 of staple plate 120 and at a second end thereof 125 to tool body 88. Spring 122 urges or pulls staple plate 120 toward the forward end 90 of tool body 88, thereby urging the column of staples 50a–50e toward the forward end 90 of tool body 88.

Referring again to FIG. 14–FIG. 16, the crimping device 86 is further provided with a pin plate 124 having a downwardly extending pin or point 126 integral with plate 124. Plate 124 is provided with a plurality of lateral legs 128 which are adapted to be received within a plurality of corresponding stabilizing grooves 130 within side walls 106 and 108. As illustrated in FIG. 14 and FIG. 16, a pin plate spring 132 is located above pin plate 124 intermediate pin plate 124 and the top 131 of tool body 88 to continually urge pin plate 124 downward away from top 131. The opposite ends of spring 132 may be appropriately secured to the top of the plate 124 and the top 131 of tool body 88. In the preferred embodiment, staple plate 124 is provided with four legs (two on each side) integral with plate 124 and side walls 106 and 108 are each provided with a pair of corresponding grooves 130.

Figures 18, 19, 20, 21:
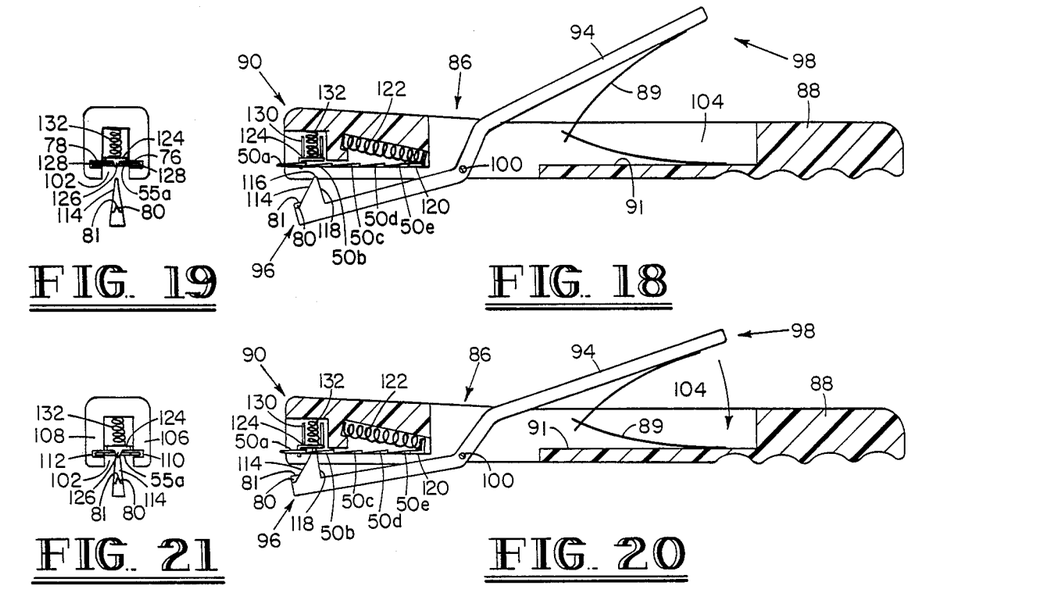
FIG. 18 is a cross-sectional schematic view of the preferred embodiment of a crimping tool illustrating the operation of the tool.
FIG. 19 is a front end schematic view of th crimping tool illustrated in FIG. 18 illustrating the operation of the tool.
FIG. 20 is a cross-sectional schematic view of the preferred embodiment of a crimping tool illustrating the operation of the tool.
FIG. 21 is a front end schematic view of the crimping tool illustrated in FIG. 20 illustrating the operation of the tool.

Referring to FIG. 18–FIG. 27, the operation of the crimping device 86 will be described. As illustrated in FIG. 18 and FIG. 19, the crimping device 86 is in the open position with staple plate 120 engaging rear staple 50e to urge a column of staples 50a–50e toward the forward end 90 of tool body 88. The column of staples 50a–50e are retained within the tool body 88 by the engagement of pin 126 with web 55a of forward staple 50a. The feet of forward staple 50a extend slightly outward from the forward end 90 and are preferably inserted to an initial depth within drilled holes 64 and 66 on opposite sides of a bone fracture line 70 by placing forward end 90 adjacent to a bone section 68. As illustrated in FIGS. 20–21, the rearward end 98 of lever arm 94 is manually urged toward tool body 88, as illustrated by the arrow in FIG. 20, thereby urging the forward end 96 of lever arm 94 between side walls 106 and 108. In this position, the pin plate abutment surface 116 will engage the underside of pin plate 124 posterior to the web 55a of forward staple 50a.

Figure 22:
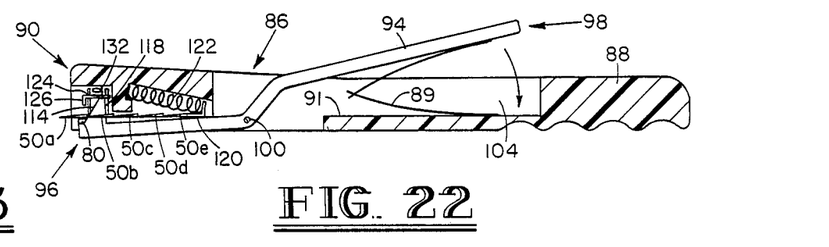
FIG. 22 is a cross-sectional schematic view of the preferred embodiment of a crimping tool illustrating the operation of the tool.
Figure 23:
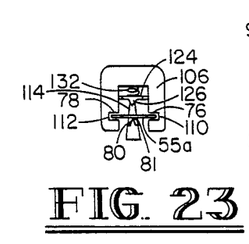
FIG. 23 is a front end schematic view of the crimping tool illustrated in FIG. 22 illustrating the operation of the tool.

As illustrated in FIGS. 22–23, the continued motion of the rearward end 98 of lever arm 94 toward tool body 88, as illustrated by the arrow in FIG. 22, causes abutment surface 116 to urge pin plate 124 upward against the downwardly biasing force of spring 132. The forward staple 50a is simultaneously urged toward the forward end 90 of tool body 88 by the engagement of crimper angle 114 with web 55a and the feet of staple 50a are urged to a final depth in the drilled holes 64 and 66 on opposite sides of a bone fracture line 70, as illustrated in FIG. 5. Likewise, the staple retaining surface 118 of lever arm 94 will engage the web 55b of the next successive staple 50b to retain the remaining staples 50b–50e within tool body 88. The apex 81 of fulcrum 80 will also abut or engage approximately the center of the web 55a of staple 50a.

Figures 24, 25:
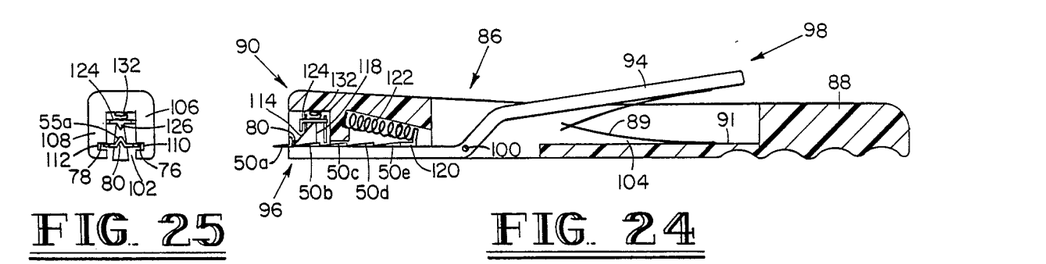
FIG. 24 is a cross-sectional schematic view of the preferred embodiment of a crimping tool illustrating the operation of the tool.
FIG. 25 is a front end schematic view of the crimping tool illustrated in FIG. 24 illustrating the operation of the tool.
Figure 26:
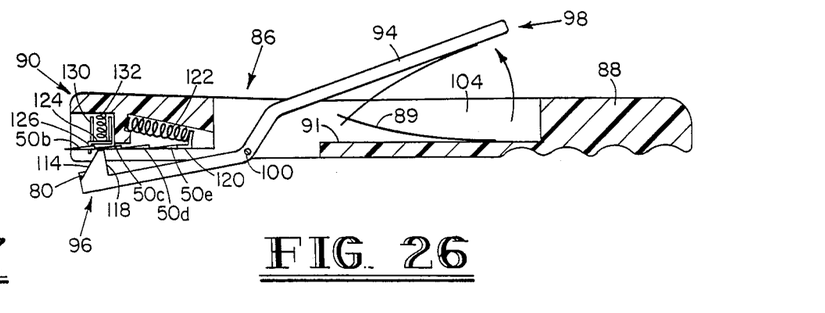
FIG. 26 is a cross-sectional schematic view of the preferred embodiment of a crimping tool illustrating the operation of the tool.
Figure 27:
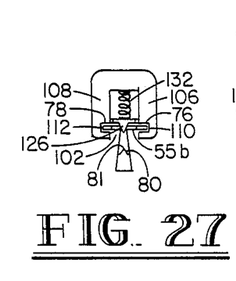
FIG. 27 is a front end schematic view of the crimping tool illustrated in FIG. 26 illustrating the operation of the tool.

Referring to FIGS. 24–25, the continued movement of forward end 96 of lever arm 94 into longitudinal slot 102 will cause abutments 76 and 78 and fulcrum 80 to bend the web 55a of forward staple 50a into substantially an inverted "V" shape, as further illustrated in FIG. 6. As illustrated in FIGS. 26–27, the subsequent movement of the rearward end 98 of lever arm 94 away from tool body 88, as illustrated by the arrow in FIG. 26, will allow abutment surface 116 to lower plate 124 and allow plate 120 and spring 122 to advance remaining staples 50b–50e toward the forward end 90 of tool body 88 until pin 126 engages the web 55b of staple 50b, thereby returning responsibility for staple retention to pin 126. Remaining staples 50b–50e may thereafter be successively crimped in a manner similar to that described in connection with staple 50a.

Figure 28:
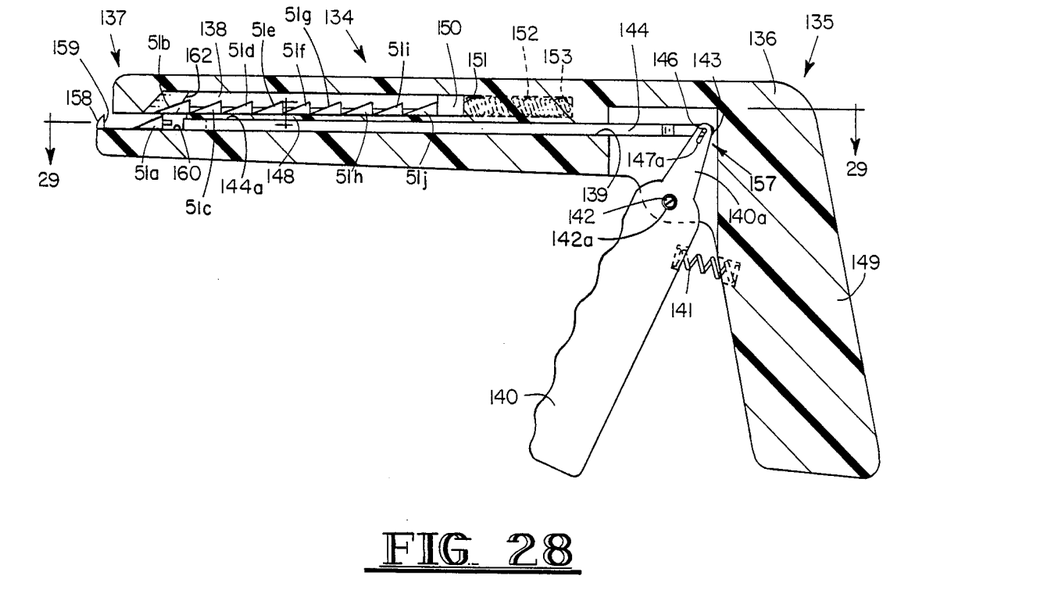
FIG. 28 is a cross-sectional view of an alternate embodiment of a crimping tool taken along section lines 28—28 of FIG. 29
Figure 29:
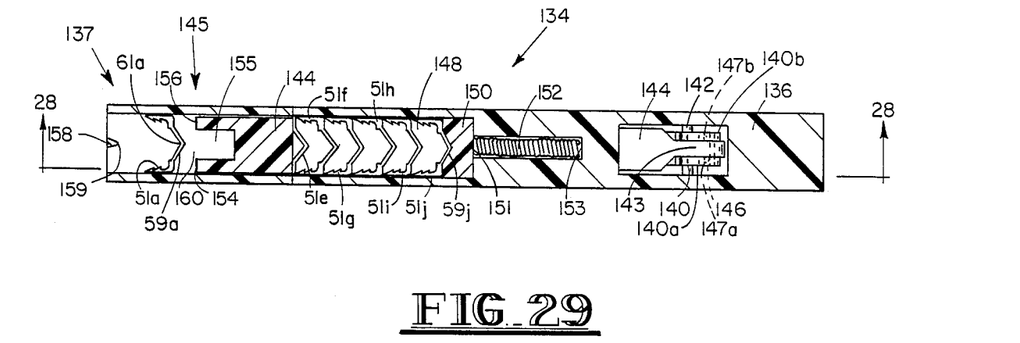
FIG. 29 is a cross-sectional view of an alternate embodiment of a crimping tool taken along section lines 29—29 of FIG. 28.
Figure 30:
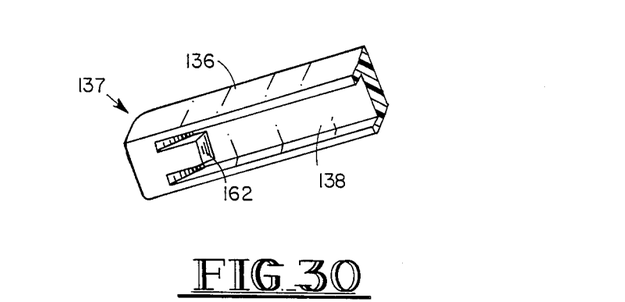
FIG. 30 is a cut away perspective view of a portion of the forward end of the crimping tool illustrated in FIG. 28.

Referring to FIGS. 28–30, an alternate staple crimping device 134 is illustrated in detail. Crimping tool 134 comprises a tool body 136 having a passage 138 therein. A trigger or lever arm 140 is pivotally connected to tool body 136 by a pivot pin 142. The opposite ends of pin 142 are connected to tool body 136. Pin 142 extends through a passage 142a in arm 140.

Referring to FIGS. 28 and 29, the upper end 157 of lever arm 140 is pivotally connected to the rearward end 143 of a push rod 144. Push rod 144 extends through a passage 139 in tool body 136 and is supported by floor 160. The rearward end 143 of push rod 144 is received between the upward prongs 140a and 140b of arm 140. A pivot pin 146 is connected to push rod 144 and extends through passages 147a and 147b in prongs 140a and 140b, respectively. A spring 141 is positioned intermediate lever arm 140 and handle 149 to bias arm 140 away from handle 149 and urge rod 144 toward the rearward end 135 of tool body 136. The opposite ends of spring 141 may be appropriately secured to arm 140 and handle 149. A table 148 is formed as part of tool body 136.

Referring again to FIG. 28, a plurality of staples 51a, 51b, 51c, 51d, 51e, 51f, 51g, 51h, 51i, and 51j, are positioned within passage 138 and each corresponds to staple 51 described hereinabove. Each staple, except staple 51a, abuts the staple immediately in front thereof. A staple plate 150 abuts the web 59j of staple 51j and is biased toward the forward end 137 of tool body 136 by means of a spring 152. Spring 152 is positioned intermediate the rear 151 of plate 150 and an inner wall 153 within tool body 136. The opposite ends of spring 152 may be appropriately secured to inner wall 153 and rear 151 of plate 150. Referring to FIGS. 29–30, the forward end 145 of push rod 144 is provided with a pair of abutments 154 and 156 having a groove 155 therebetween. The forward end 137 of tool body 136 is provided with a fulcrum 158 having an apex 159. Tool body 136 is also provided with an angled camming surface 162.

Prior to usage of the tool 134, a strap or clasp (not shown) is positioned about trigger 140 and handle 149 so as to squeeze trigger 140 and handle 149 together and urge push rod 144 toward the forward end 137 of tool body 136. In such a mode, forward staple 51a is supported by upper surface 144a of push rod 144 and staples 51b–51j are supported by table 148 and urged toward the forward end 137 of tool body 136 by plate 150. However, when the strap (not shown) is removed, spring 141 will urge trigger 140 away from handle 149, as illustrated in FIG. 28, thereby urging push rod 144 toward the rearward end 135 of tool body 136. When the push rod 144 is withdrawn toward the rearward end 135 of tool body 136, as illustrated in FIG. 28, the forward staple 51a is urged downward to the floor 160 of passage 138 by the urging of plate 150 and the engagement of the shoulders of staple 51a with angled camming surface 162. The remaining staples 51b–51j are likewise advanced forward at the urging of plate 150. As staple 51b advances and engages camming surface 162, its forward progress ceases when its body encounters the body of staple 51a. As push rod 144 and staple 51a advance toward the forward end 137 of tool body 136, responsibility for supporting staple 51b shifts from staple 51a to support surface 144a of push rod 144.

When forward end 137 is placed adjacent to a bone section 68, staple 51a is received atop floor 160, and the push rod 144 is urged toward the forward end 137 of tool body 136 by manually operated trigger 140, movable abutments 154 and 156 will engage staple 51a and push staple 51a along floor 160 until the feet thereof are received within drilled holes 64 and 66 on opposite sides of a bone fracture line 70 and apex 159 abuts vertex 61a in approximately the center of staple 51a, as illustrated in FIG. 9. The web 59a is sufficiently angled to allow the feet of staple 51a to be fully inserted into the drilled holes 64 and 66 prior to the crimping of staple 51a. Movement of abutments 154 and 156 about fulcrum 158 by means of trigger 140 will crimp the staple 51a, as further illustrated in FIG. 10. push rod 144 may thereafter be withdrawn toward the rear 135 of tool body 136 to permit the next staple 51b to be received atop floor 160 at the urging of plate 150 and engagement of camming surface 162 with the shoulders of staple 51b. The remaining staples 51c–51j are likewise advanced forward at the urging of plate 150 until staple 51c encounters staple 51b. The tool 134 is then ready to crimp staple 51b in a manner as described in connection with staple 51a. Tool 134 will also operate in a similar manner to successively crimp staples 51c-51j.

Figure 31:
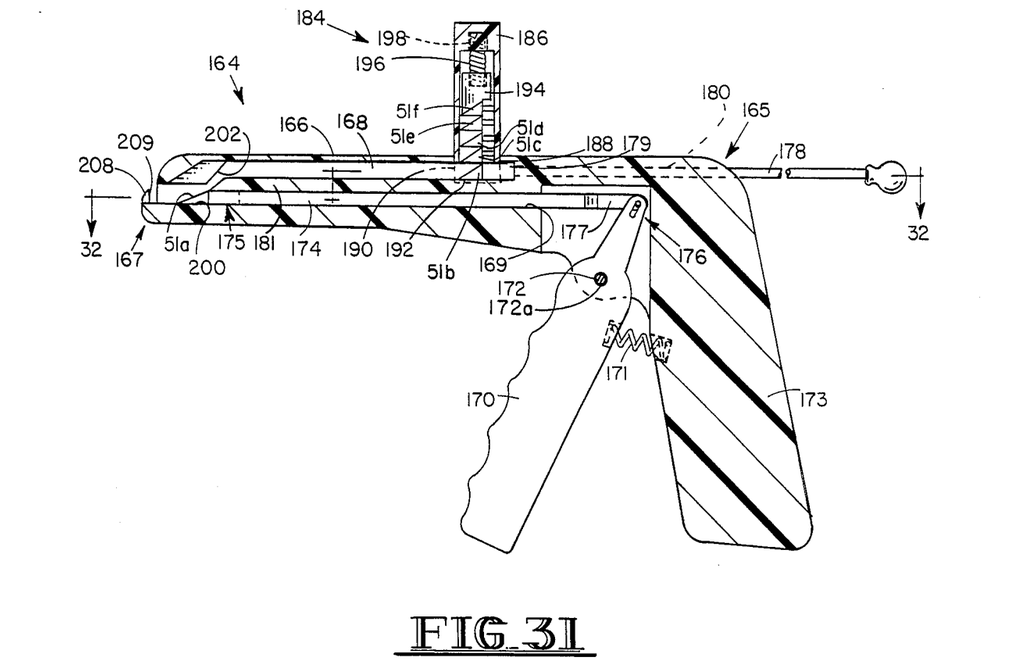
FIG. 31 is a cross-sectional view of an alternate embodiment of a crimping tool taken along section lines 31—31 of FIG. 32.
Figure 32:
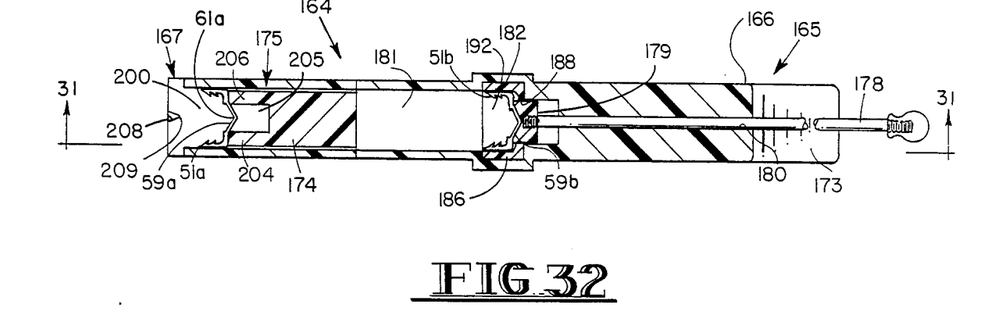
FIG. 32 is a cross-sectional view of an alternate embodiment of a crimping tool taken along section lines 32—32 of FIG. 31.
Figure 33:
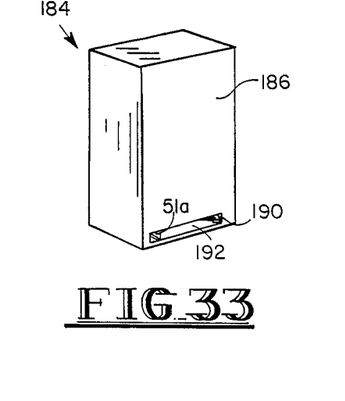
FIG. 33 is a front perspective view of the staple cartridge illustrated in FIG. 31.
Figure 34:
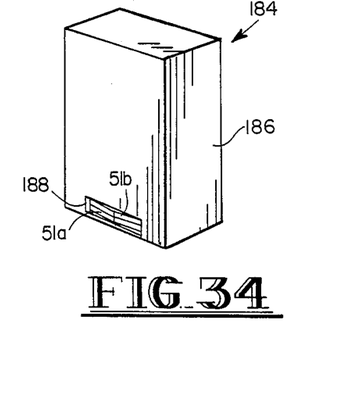
FIG. 34 is a rear perspective view of the staple cartridge illustrated in FIG. 31.

Referring to FIG. 31 and FIG. 32, an alternate crimping device 164 is illustrated in detail. The crimping device 164 comprises a tool body 166 having a passage 168 therein. A trigger or lever arm 170 is pivotally connected to tool body 166 by a pivot pin 172. The opposite ends of pin 172 are connected to tool body 166. Pin 172 extends through a passage 172a in arm 170. A first push rod 174 extends through a passage 169 in tool body 166 and is supported by floor 200. The rearward end 177 of push rod 174 is designed like rearward end 143 of push rod 144, upper end 176 of lever arm 170 is designed like upper end 157 of trigger 140, and push rod 174 and lever arm 170 are pivotally connected in a manner as described in connection with push rod 144 and trigger 140. A second push rod 178 having a push plate 179 connected thereto extends through a passage 180 in tool body 166. A spring 171 is positioned intermediate lever arm 170 and handle 173 to urge push rod 174 toward the rearward end 165 of tool body 166. The opposite ends of spring 171 may be appropriately secured to trigger 170 and handle 173. A staple support table 181 is formed as part of tool body 166.

Referring to FIGS. 31-34, the uppermost surface of tool body 166 is provided with a cavity 182 within which to receive a staple cartridge 184. Staple cartridge 184 comprises a housing 186 having a rearward slot 188 on the lowermost end thereof and a forward slot 190 on the lowermost end thereof substantially aligned with slot 188. A stack of bone staples 51a, 51b, 51c, 51d, 51e and 51f, each of which corresponds to staple 51 described hereinabove, are positioned within the cartridge 184 prior to usage thereof and biased toward the floor 192 of housing 186 by a plate 194. Each staple within cartridge 184, except the lowermost staple, abuts the staple immediately therebelow. Plate 194 is likewise biased toward floor 192 by means of tension spring 196 intermediate plate 194 and the upper wall 198 of housing 186. The opposite ends of spring 196 may be appropriately secured to plate 194 and upper wall 198.

Referring again to FIG. 31 and FIG. 32, the staple cartridge 184 is inserted into cavity 182 and the lowermost staple 51a is urged toward the forward end 167 of tool body 166 atop table 181 by means of push rod 178 and push plate 179. Plate 179 is inserted through rearward passage 188 in cartridge housing 186 to engage the web 59a of lowermost staple 51a. Plate 179 and staple 51a are thereafter pushed through forward passage 190 toward forward end 167 of tool body 166. The staple 51a is urged toward the forward end 167 of tool body 166 until it is urged downward toward floor 200 by the engagement of the shoulders of staple 51a with an angled camming surface 202. Camming surface 202 is formed as a part of tool body 166 and is similar to the camming surface 162 illustrated in FIG. 30. The push rod 178 may thereafter be withdrawn so as to allow staple 51b to be received atop floor 192 and to engage plate 179 with web 59b of staple 51b, as illustrated in FIGS. 31-32.

As illustrated in FIG. 32, the forward end 175 of first push rod 174 is provided with a pair of abutments 204 and 206 having a groove 205 therebetween. The forward end 167 of tool body 166 is provided with a fulcrum 208 having an apex 209. When a staple, such as staple 51a, rests atop floor 200 and forward end 167 is placed adjacent to a bone section 68, push rod 174 is urged toward the forward end 167 of tool body 166 by manually operated trigger 170. Movable abutments 204 and 206 will thereby engage staple 51a and push staple 51a along floor 200 until the feet of staple 51a are received within holes 64 and 66 in bone section 68 and apex 209 abuts vertex 61a in approximately the center of staple 51a. Once again, the web 59a is sufficiently angled to allow the feet of staple 51a to be fully inserted into holes 64 and 66 prior to the crimping of staple 51a. Movement of abutments 204 and 206 about fulcrum 208 by means of trigger 170 will cause the staple 51a to be crimped in a manner as illustrated in FIG. 10. Tool 164 will also operate in a similar manner to successively crimp staples 51b-51f.

Figures 35, 36, 37, 38, 39, 40, 41, 42:
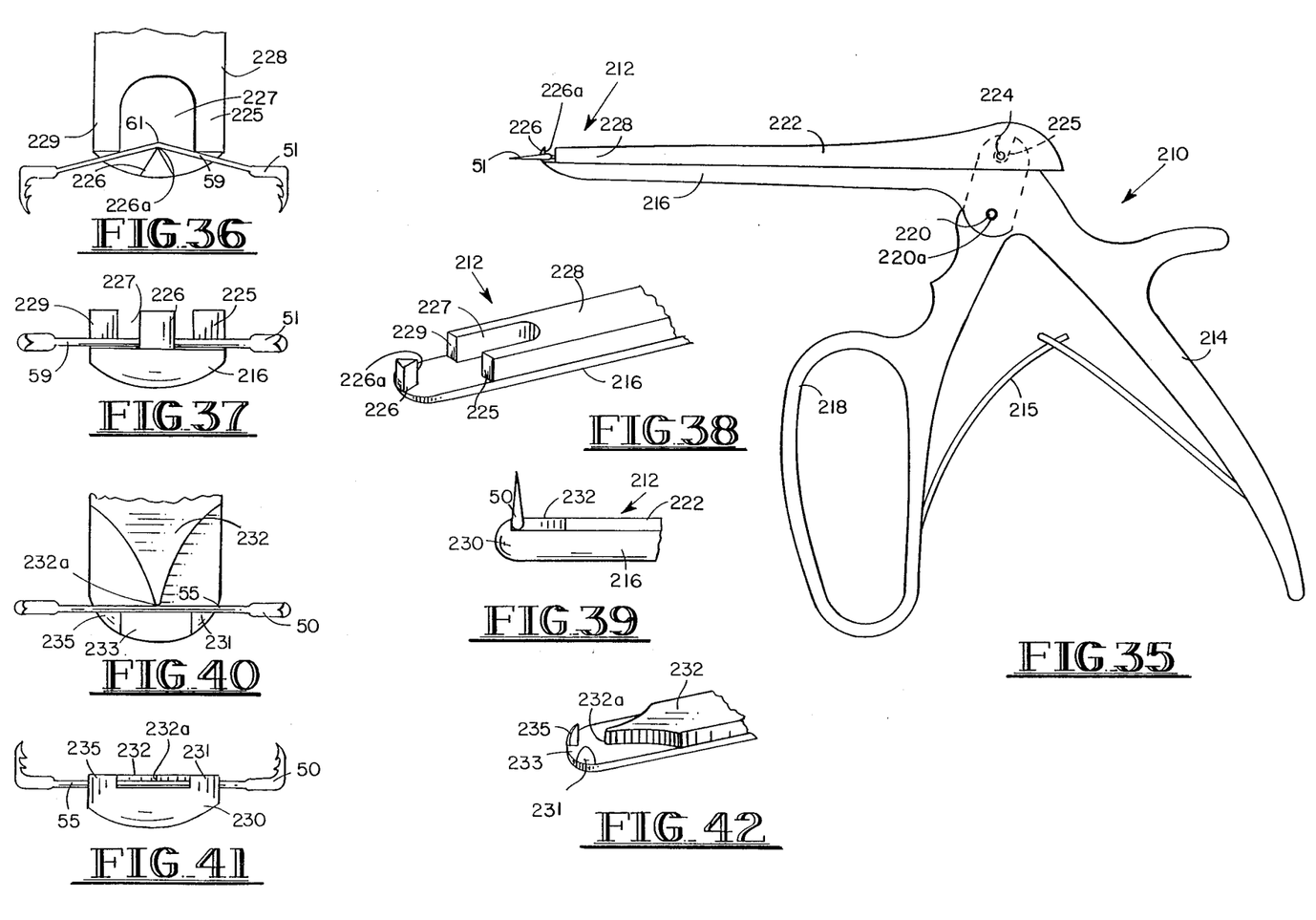
FIG. 35 is a side view of an alternate embodiment of a crimping device adapted to crimp a single staple.
FIG. 36 is a top view of the forward end of the crimping device illustrated in FIG. 35.
FIG. 37 is a front end view of the forward end of the crimping device illustrated in FIG. 35.
FIG. 38 is a perspective view of the forward end of the crimping device illustrated in FIG. 35.
FIG. 39 is a side view of the forward end of another embodiment of a crimping device adapted to crimp a single staple.
FIG. 40 is a top view of the forward end of a crimping device illustrated in FIG. 39.
FIG. 41 is a front end view of the forward end of a crimping device illustrated in FIG. 39.
FIG. 42 is a perspective view of the forward end of a crimping device illustrated in FIG. 39.

An alternate crimping device 210 having a forward end 212 adapted to crimp a single staple is illustrated in FIG. 35. The crimping device 210 comprises a handle 214 having a stationary arm 216 formed as an integral part thereof. A trigger 218 is pivotally connected to handle 214 by pivot pin 220. Pin 220 is connected to handle 214 and extends through a passage 220a in trigger 218. A spring 215 is positioned intermediate handle 214 and trigger 218 and connected to handle 214 and trigger 218 by rivets (not shown). Trigger 218 is connected to a sliding arm 222 by means of a pin 224 which is connected to arm 222 and is received within a groove or passage 225 in trigger 218. Arm 222 is in sliding engagement with arm 216.

As illustrated in FIGS. 36-38, the forward end of arm 216 is provided with an integral fulcrum 226 having an apex 226a and the forward end of arm 222 is provided with an integral buttress 228. Buttress 228 defines a pair of abutments 225 and 229 having a cavity 227 therebetween. The embodiment of the crimping device 210 illustrated in FIGS. 35-38 comprises a forward action model wherein a staple 51 is positioned between the fulcrum 226 and buttress 228. In this position, the feet of staple 51 may be inserted into holes 64 and 66 in bone section 68. Once again, web 59 is sufficiently angled to allow the feet of staple 51 to be uully inserted into holes 64 and 66 prior to crimping staple 51. Squeezing the trigger 218 advances arm 222 and buttress 228. Advancement of the buttress 228 will compress the web 59 of staple 51 against fulcrum 226, thereby crimping the web 59 in a manner as illustrated in FIG. 10. For the sake of clarity, no staple 51 is illustrated in FIG. 38.

FIGS. 39-42 illustrate an alternate embodiment of the forward end 212 of device 210 adapted to crimp a staple 50. The forward end of arm 216 is provided with an integral buttress 230 and the forward end of arm 222 is provided with an integral fulcrum 232 having an apex 232a. Buttress 230 defines a pair of abutments 231 and 235 having a cavity 233 therebetween. The embodiment of the crimping device illustrated in FIGS. 39-42 comprises an up action model wherein a staple 50 is positioned between the buttress 230 and fulcrum 232. In this position, the feet of staple 50 may be inserted into holes 64 and 66 in bone section 68. Squeezing the trigger 218 advances arm 222 and fulcrum 232 while the web 55 of staple 50 is stabilized against buttress 230. Advancement of fulcrum 232 will crimp the web 55 of staple 50 in a manner as illustrated in FIG. 6. For the sake of clarity, no staple 50 is illustrated in FIG. 42.

Figure 43:
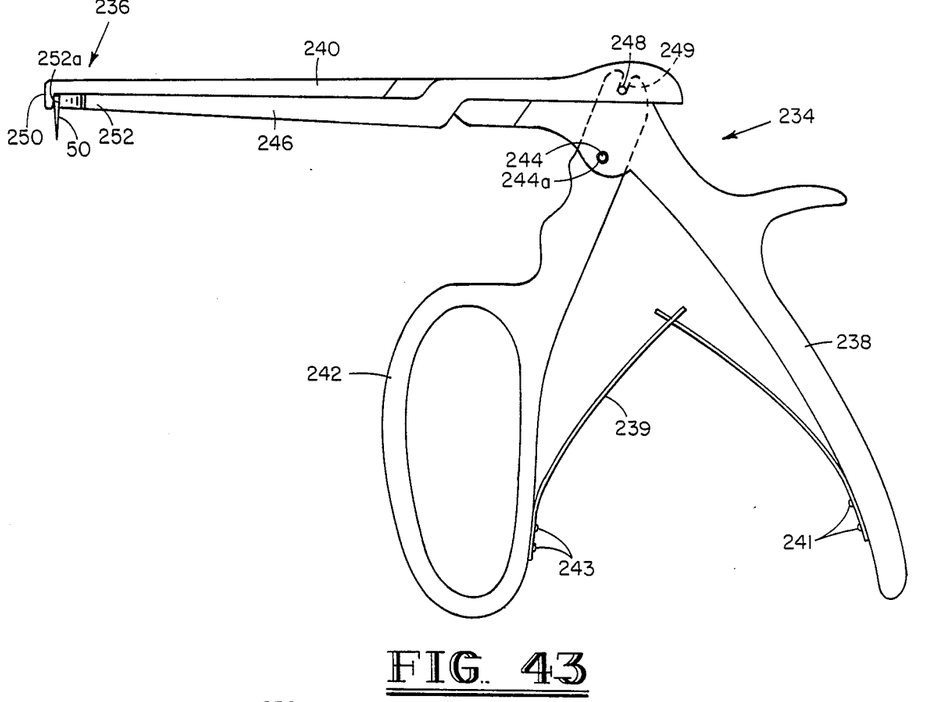
FIG. 43 is a side view of a further embodiment of a crimping device adapted to crimp a single staple.

An alternate crimping device 234 having a forward end 236 adapted to crimp a single staple 50 is illustrated in FIG. 43. The crimping device 234 comprises a handle 238 having a stationary arm 240 formed as an integral part thereof. A trigger 242 is pivotally connected to handle 238 by pivot pin 244. Pin 244 is connected to handle 238 and extends through a passage 244a in trigger 242. A spring 239 is positioned intermediate handle 238 and trigger 242 and connected to handle 238 and trigger 242 by rivets 241 and 243, respectively. Trigger 242 is connected to a sliding arm 246 by means of a pin 248 which is connected to arm 246 and is received within a groove or passage 249 in trigger 242. Arm 246 is in sliding engagement with arm 240.

Figure 44:
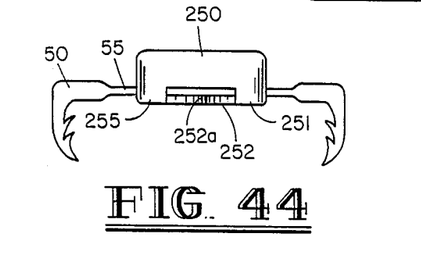
FIG. 44 is a front end view of the forward end of the crimping device illustrated in FIG. 43.
Figure 45:
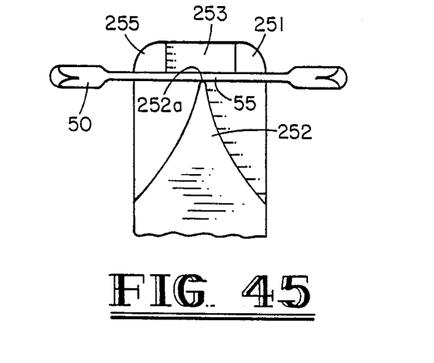
FIG. 45 is a bottom view of the forward end of the crimping device illustrated in FIG. 43.

As illustrated in FIG. 44 and FIG. 45, the forward end of arm 240 is provided with an integral buttress 250 and the forward end of arm 246 is provided with a fulcrum 252 having an apex 252a. Buttress 250 defines a pair of abutments 251 and 255 having a cavity 253 therebetween. The embodiment of the crimping device 234 illustrated in FIGS. 43-45 comprises a down action model wherein a staple 50 is positioned between the buttress 250 and fulcrum 252. In this position, the feet of staple 50 may be inserted into holes 64 and 66 in bone section 68. Squeezing the trigger 242 advances arm 246 and fulcrum 252 while the web 55 of staple 50 is stabilized against buttress 250. Advancement of the fulcrum 252 will crimp the web 55 of staple 50 in a manner as illustrated in FIG. 6.

It is to be understood that staple 50, having a generally straight central portion 55, will normally be used in the method illustrated in FIGS. 5-8 and in connection with a crimping device wherein a fulcrum moves relative to a pair of abutments, such as the crimping devices illustrated in FIGS. 13, 39 and 43. Staple 51, having an angled web 59 and a vertex 61, will normally be used in the method illustrated in FIGS. 9-12 and in connection with a crimping device wherein a pair of abutments move relative to a fulcrum, such as the crimping devices illustrated in FIGS. 28, 31, and 35. It is also to be understood that the "V" shaped crimped portion of staples 50 and 51, as illustrated in FIGS. 7 and 11, respectively, extends away from the respective feet 53 and 58. Further, it is to be understood that web 55 of staple 50 may extend between feet 53 and 58 and that angled web 59 of staple 51 may extend between feet 53 and 58. It is also to be understood that the various abutments and fulcrums disclosed herein to crimp staples 50 or 51 are preferably constructed of surgical grade metal, such as stainless steel. Finally, it is to be understood that staples 50 and 51 and the various crimping devices disclosed herein are preferably sterilized prior to surgical usage.

While the method and apparatus for interosseous bone fixation has been described in connection with the preferred embodiment, it is not intended to limit the invention to the particular form set forth, but on the contrary, it is intended to cover such alternatives, modifications, and equivalents, as may be included within the spirit and scope of the invention, as defined by the appended claims.

I claim:
1. A method for bone fixation, comprising the steps of:
 (a) inserting first and second feet of a bone staple into first and second drill holes, respectively, in a section of bone, said first drill hole located on a first side of a fracture line in said bone section and said second drill hole located on a second side of said fracture line;
 (b) crimping a web of said staple into substantially an inverted V shape, said crimping step providing an initial compression of said bone portions toward each other;
 (c) compressing said crimped portion of said staple web, said compressing step providing a second compression of said bone portions toward each other; and
 (d) folding said compressed portion of said staple web toward one side of said fracture line.

2. A method for fixating a first bone portion and a second bone portion, comprising the steps of:
 (a) inserting a first foot and second foot of a bone staple into said first bone portion and said second bone portion, respectively, said first foot and said second foot being substantially perpendicular to a central portion of said staple;
 (b) crimping said central portion of said staple into substantially an inverted V shape and in a plane substantially perpendicular to the plane of said first foot and said second foot so as to cause said first foot to impart compressive forces to said first bone portion in a first direction toward said second foot and simultaneously cause said second foot to impart compressive forces to said second bone portion in a second direction toward said first foot, said crimping step providing an initial compression of said bone portion toward each other; and
 compressing said crimped central portion so as to cause said first foot to impart compressive forces to said first bone portion in a first direction toward said second foot and simultaneously cause said second root to impart compressive forces to said second bone portion in a second direction toward said first foot, said compressing step providing a second compression of said bone portions toward each other.

3. A method for fixating a first bone portion and a second bone portion, as recited in claim 2, further comprising the step of drilling first and second holes in said first and second bone portions, respectively, prior to said step of inserting said first foot into said first bone portion and said second foot into said second bone portion.

* * * * *